US005239994A

United States Patent [19]
Atkins

[11] Patent Number: 5,239,994
[45] Date of Patent: Aug. 31, 1993

[54] JET VENTILATOR SYSTEM
[75] Inventor: Roger L. Atkins, Salt Lake City, Utah
[73] Assignee: Bunnell Incorporated, Salt Lake City, Utah
[21] Appl. No.: 698,297
[22] Filed: May 10, 1991
[51] Int. Cl.$^5$ ............................................. A61M 16/00
[52] U.S. Cl. ............................ 128/204.18; 128/204.25
[58] Field of Search ...................... 128/204.24, 204.25, 128/207.14, 207.15, 207.16, 204.18

[56] References Cited
U.S. PATENT DOCUMENTS

| | | | |
|---|---|---|---|
| 4,520,812 | 6/1985 | Freitag et al. | 128/204.25 |
| 4,565,194 | 1/1986 | Weerda et al. | 128/204.25 |
| 4,573,462 | 3/1986 | Baum | 128/207.15 |

Primary Examiner—Edgar S. Burr
Assistant Examiner—Aaron I. Lewis
Attorney, Agent, or Firm—Thorpe North & Western

[57] ABSTRACT

A jet ventilator system for assisting a person's respiration includes a source of gas under pressure, a tracheal tube for insertion into the mouth and throat of the person, a jet nozzle disposed in the tracheal tube for directing gas pressure pulses toward the end of the tracheal tube inserted into the person's mouth, a primary delivery conduit coupled between the source of gas and the tracheal tube for delivering gas under pressure to the jet nozzle, a control unit coupled to the primary delivery conduit for selectively varying the flow rate through the jet nozzle, and an exhaust conduit coupled to the tracheal tube for carrying air exhaled by the person. The control unit includes a control delivery conduit coupled between the primary delivery conduit and the tracheal tube for delivering gas under pressure from the primary delivery conduit to the tracheal tube to a location near the jet nozzle, and an inhalation valve disposed in the control delivery conduit for selectively varying the pressure of gas flowing through the control delivery conduit to the tracheal tube and thus the gas flow rate through the jet nozzle. In this manner the inhalation valve controls the pressure pulses, both magnitude and frequency, present in the tracheal tube which are providing the ventilation for the person.

8 Claims, 3 Drawing Sheets

JET VENTILATOR SYSTEM

BACKGROUND OF THE INVENTION

This invention relates to a new and improved system for injecting bursts or jets of air into a person's respiratory system to assist ventilation and respiration.

The mechanical application of positive pressure pulses of oxygen and air to a person's respiratory system has become fairly routine in neonatal, pediatric and adult intensive care facilities. With the more conventional ventilators, relatively large volumes of oxygen and air are applied to a person's respiratory system at frequencies which coincide generally with the normal inhalation frequency of the person. Another type of ventilator, known as a volume ventilator and typically used in adult and pediatric intensive care facilities, may operate in modes which apply the oxygen and air at fixed time intervals, or in modes that use respiratory effort to trigger the application of the oxygen and air.

Neonatal intensive care facilities typically use time-cycled, pressure-limited ventilators which provide a generally constant bias flow of fresh gas (oxygen and air) through a patient breathing circuit attached to the infant's respiratory system. FIG. 1 shows a pneumatic diagram of a typical prior art time-cycled, pressure-limited ventilator in which the pressure behind a diaphragm 2 in an exhalation valve 4 controls the pressure of gas in a tube 8, inserted into the infant's trachea. This diaphragm occludes the exit of exhaled gas from the patient breathing circuit shown in FIG. 1 until the pressure within the breathing circuit feed tube 8 exceeds the pressure behind the diaphragm 2, at which time gas is allowed to escape via discharge tube 12. Mechanical ventilation of the infant's respiratory system is provided by varying the exhalation valve 4 diaphragm pressure between a low value, called positive end-expiratory pressure (PEEP), and a high value, called the pressure limit. The ventilator of FIG. 1 cycles the application of gas to the infant at a fixed ventilation rate and for a fixed duration of time based on settings chosen by the operator. Attempts have been made to produce neonatal ventilators which trigger the delivery of gas to the infant based on respiratory effort, but because of difficulties in detection (in infants) and timely response, such attempts have generally proven unsuccessful. Still, it would be desirable to combine volume ventilators and neonatal time cycled/pressure limited ventilators into one unit so that the unit could be used either for pediatric intensive care or neonatal intensive care.

In addition to the conventional ventilator approach in which oxygen and air are applied to a person's respiratory system at frequencies generally coinciding with normal inhalation frequencies, it has been found that persons with various respiratory problems and illnesses can be benefited by the application of rapid, positive pressure pulses of oxygen and air to the persons' respiratory system. Examples of apparatus and methods of applying positive pressure pulses of gas to a patient at a higher than normal rate of inhalation and exhalation are disclosed in U.S. Pat. Nos. 4,481,944 and 4,538,604, and the references cited therein. Of course, such ventilators are not suitable for all respiratory problems and so if complete respiratory care is to be provided, both the rapid pulse ventilator and conventional ventilator would be necessary.

SUMMARY OF THE INVENTION

It is an object of the invention to provide a ventilator system for more efficiently applying positive pressure pulses of oxygen and air to ventilate a person's respiratory system.

It is also an object of the invention to provide such a system in which oxygen and air is injected and jetted toward the patient's respiratory system.

It is a further object of the invention to provide a ventilator system capable of combining conventional low frequency ventilation with high frequency ventilation, for delivery through a single tracheal tube.

It is an additional object of the invention to provide such a system which may be utilized either for pediatric ventilation or neonatal ventilation.

It is another object of the invention to provide such a system in which the mechanical dead space in the breathing circuit may be reduced, and thus the rebreathing of exhaled gas is likewise reduced.

The above and other objects of the invention are realized in a specific illustrative embodiment of a jet ventilator system which includes a source of gas under pressure, a tracheal conduit, one end of which is for insertion into the mouth and throat of a patient, a jet nozzle disposed in the other end of the conduit for directing gas under pressure toward the one end of the conduit, and a primary delivery conduit coupled between the source of gas and the other end of the tracheal conduit for delivering gas under pressure to the jet nozzle. A control unit is coupled to the primary delivery conduit for selectively varying the flow rate through the jet nozzle. An exhaust conduit is coupled at one end to the tracheal conduit for carrying away air exhaled by the patient.

In accordance with one aspect of the invention, the control unit includes a control delivery conduit coupled between the primary delivery conduit and the other end of the tracheal conduit for delivering gas under pressure from the primary delivery conduit to the tracheal conduit to a location near the jet nozzle. The control unit also includes an inhalation valve disposed in the control delivery conduit and responsive to control signals for varying the pressure of gas flowing through the control delivery conduit to the tracheal conduit, and thus the gas flow rate through the jet nozzle. A control signal source selectively produces control signals for supply to the inhalation valve to thereby control the variation of pressure of gas flowing through the control delivery conduit. By appropriate production of control signals, either conventional ventilation rates, high frequency jet ventilation rates, or a combination of conventional ventilation and high frequency ventilation rates may be developed, all with one system.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
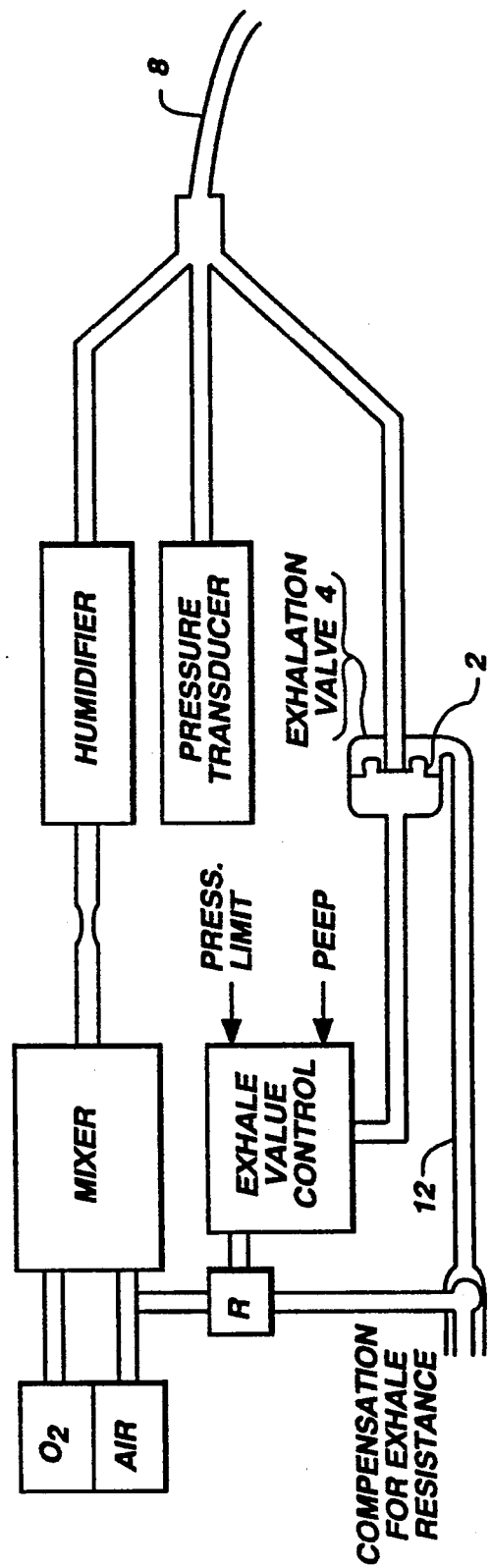
FIG. 1 is a pneumatic diagram of a conventional time-cycled, pressure-limited ventilator.

As briefly described earlier, FIG. 1 shows a schematic of a conventional time-cycled, pressure-limited ventilator used in neonatal intensive care facilities.

Figure 2:
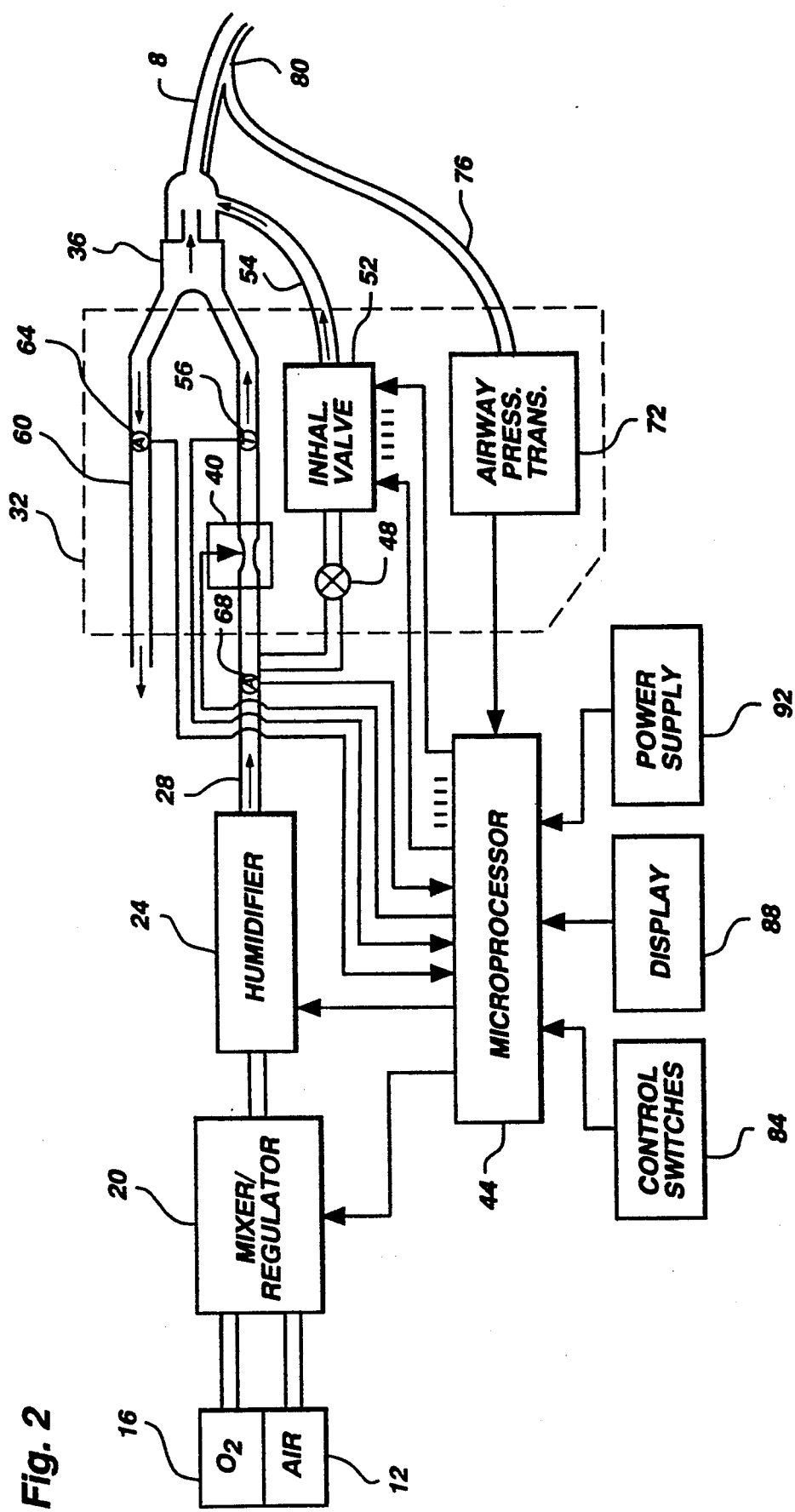
FIG. 2 is a pneumatic diagram of a jet ventilator system made in accordance with the principles of the present invention.

FIG. 2 shows a schematic of a system for applying a series of gas pressure pulses to a patient's respiratory system through a gas jet nozzle 4. The gas jet nozzle 4 is disposed in one end of a tracheal tube 8, the other end of which is for insertion into the patient's mouth in a conventional fashion. The tracheal tube 8 would be configured in a variety of sizes such that it would be long enough and narrow enough for easy insertion into the mouth and throat of a patient, either adult, child or infant.

The system of FIG. 2 also includes separate sources 12 and 16 of air and oxygen respectively, which are supplied to a mixer/regulator 20 where the air and oxygen are mixed to the desired concentration and regulated to a constant supply pressure, for example, about 20 psi. The mixed gas is then heated and humidified in a humidifier 24 to a temperature and humidity of about 37 degrees centigrade and 100 percent RH (after the gas is allowed to expand to near ambient pressures used for ventilation). The apparatus thus far described is all conventional for ventilators.

From the humidifier 24, the gas flows via a primary delivery conduit 28 to a patient box 32 containing gas flow control devices to be discussed momentarily. The patient box 32 is disposed so as to be fairly close to a patient to better control the flow rate and pressure of gas supplied to the patient. The patient box 32 is coupled via a manifold 36 to the gas jet nozzle 4, previously described.

The patient box 32 contains a variable restrictor 40 which is operated under control of a microprocessor 44 to control the bias (or base) flow of gas toward the gas jet nozzle 4, a pinch valve 48 which can be used to stop the flow of gas through the gas jet nozzle 4, and an inhalation valve 52 which also operates under control of the microprocessor 44 to control the gas flow rate through the gas jet nozzle 4. The pinch valve 48 and inhalation valve 52 are coupled in series in a control delivery conduit 54 which connects the primary delivery conduit 28 to the tracheal conduit 8 at a location near the gas jet nozzle 4. A thermistor 56 is disposed in the primary delivery conduit between the variable restrictor 40 and the manifold 36, for measuring the temperature of gas in the primary delivery conduit 28. Coupled to the manifold 36 is an exhaust conduit 60 in which is disposed an anemometer 64 for measuring flow of gas (expired from the patient) through the exhaust conduit. Another anemometer 68 is disposed in the primary delivery conduit 28 between the humidifier 24 and the variable restrictor 40 for measuring the flow of gas from the humidifier to the variable restrictor. The two anemometers 64 and 68 and the thermistor 56 are all coupled to the microprocessor 44 which periodically reads and records measurements made by the identified devices for purposes to be described momentarily.

Also included in the patient box is an airway pressure transducer 72 coupled by way of a connecting tube 76 to a lumen 80 formed in the tracheal conduit 8. As the name indicates, the airway pressure transducer 72 detects the pressure in the tracheal conduit 8, and thus the pressure in the patient's tracheal airway, and provides a signal (representing the pressure) to the microprocessor 44.

Coupled to the microprocessor 44 are control switches 84 by which input signals, for example for setting pressure levels and frequencies of gas pressure pulses, may be supplied to the microprocessor, a display unit 88 for displaying various parameters associated with the system, and a power supply unit 92 for supplying power to the microprocessor and other elements in the system.

Figure 3A:
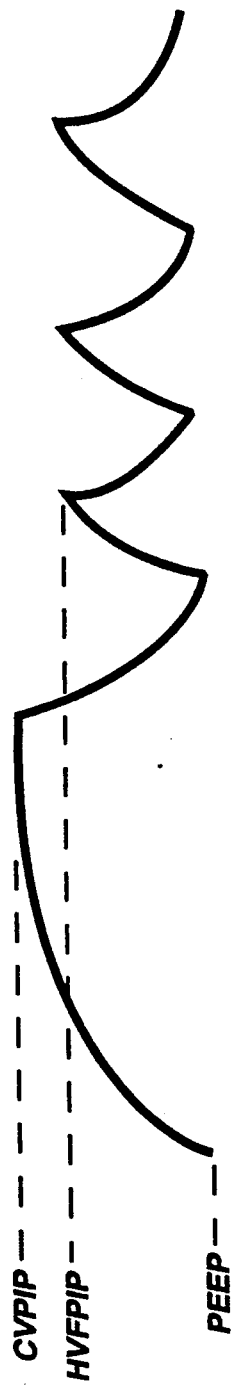
FIGS. 3A and 3B show respectively a conventional ventilator airway pressure waveform followed by a high frequency ventilator airway pressure waveform, and a stacked ventilator airway pressure waveform constituting the sum of conventional and high frequency ventilator airway pressure waveforms.
Figure 3B:
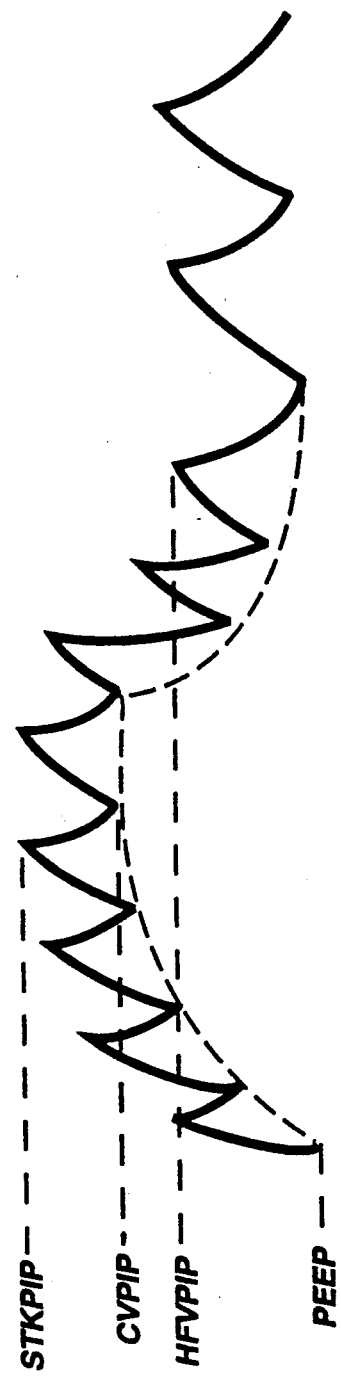

Since the air pressure in the tracheal conduit 8 is directly related to the flow rate through the gas jet nozzle 4, controlling such flow rates, i.e. transitioning between different flow rates, allows for controlling and transitioning between air pressures in the tracheal conduit 8. In particular, the inhalation valve 52, in response to signals from the microprocessor 44, controls the delivery of air through the control delivery tube 54 to allow for rapid transitions between various and different inspired gas flow rates and thus various and different air pressures in the tracheal conduit 8. For example, four pressure levels may be selected by appropriate settings of the inhalation valve 52, these four pressure levels being (1) positive end-expiratory pressure (PEEP), (2) conventional ventilation peak-inspiratory pressure (CVPIP), (3) high frequency ventilation peak-inspiratory pressure (HFVPIP), and (4) peak-inspiratory pressure resulting from stacking or superimposing high frequency ventilation over conventional ventilation breaths (STKPIP). These various pressures are illustrated (and labeled) diagrammatically in FIGS. 3A and 3B for an exemplary operation cycle of the inhalation valve 52. As already indicated, these four pressures may be independently selected by the operator and synthesized by the jet ventilator system.

An exemplary inhalation valve structure suitable for independently developing the four pressure levels indicated is disclosed in copending U.S. patent application Ser. No. 07/698,705, filed May 10, 1991. In general, such inhalation valve structure utilizes a flexible tube positioned for pinching by two independently operated moveable pinchers, under control of the microprocessor 44. Each of the two pinchers may be moved to two different positions relative to the flexible tube to thereby provide four pinching configuration combinations for the flexible tubing.

One of the moveable pinchers of the inhalation valve 52 is used to deliver ventilation at conventional rates and the other pincher is used to deliver high frequency ventilation. Thus, if only the first mentioned pincher is operated, then ventilation will be provided at only the conventional rate, or if only the other pincher is operated, then ventilation will be provided only at the high frequency rate. If both pinchers are operated, then a combination or superimposed conventional rate and high frequency rate are provided simultaneously, such a pressure waveform being shown in FIG. 3B.

In the manner described, the inhalation valve 52 controls gas flow in the tracheal conduit 8, both as to pressure levels and to frequency of changes in the pressure levels. The inspired gas flow is introduced to the tracheal conduit 8 through the jet nozzle 4 and is "jetted" toward the patient. Because the patient's airway pressure equilibrates at a value sufficient to halt the inspired gas jet at some point, the momentum of the inspired gas jet is converted to the pressures required for ventilating the patient's respiratory system.

Exhaled gases from the patient flow through the tracheal conduit 8 and out the exhaust conduit 60. The exhaust conduit 60 serves not only as an exit for exhaled gases, but also as a reservoir of fresh gas for spontaneous breathing by the patient, and as a muffler to reduce the noise created by the inspired gas jet.

The thermistor 56 located in the primary delivery tube 28, provides a measure of the temperature of the inspired gas. This information may be used by the microprocessor 44 for control of heaters in the humidifier 24 and in the patient breathing circuit wherever such heaters might be located.

The anemometers 64 and 68 measure the gas flow rates from the patient and to the patient respectively, the difference of the two measurements thus representing the net gas flow to the patient. The microprocessor 44 integrates this information to determine tidal volumes, and may be used to trigger mechanical ventilation and synchronization with respiratory effort. Another use of this information would be to detect slippage of the tube 8 from the patient (in which case the gas flow rate from the patient would be zero while the gas flow rate to the patient would still be high), or to determine the magnitude of air leaks such as might occur around the tube 8.

Among the advantages of the above-described jet ventilator system are a more rapid delivery of gas pressure pulses and lower exhalation resistance than with conventional methods. Also, as already described, the jet ventilator system may deliver gas pressure pulses at both conventional ventilation rates and high frequency ventilation rates. Since a single unit can deliver gas pressure pulses at both rates, less equipment is needed to treat a broad range of respiratory problems and so lower costs are achieved. Further, infant or neonatal respiration assistance can be provided with the system as well as adult and pediatric respiration assistance. Finally, mechanical dead space within the breathing circuit is substantially eliminated with the system and so the rebreathing of gas is reduced and smaller tidal volumes may be used to achieve the desired gas exchange. (Mechanical dead space is occupied by exhaled gases when the exhalation time is insufficient for the system to reach equilibrium so that the patient's PEEP is higher than the ventilator's PEEP setting. The gas volume in the tracheal tube is therefore not replaced with fresh gas between breaths and so some of the exhaled gas is rebreathed. Of course, rebreathing the gas dilutes the oxygen concentration of the inspired gas thereby lowering effectiveness.)

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

I claim:

1. Jet ventilation apparatus for assisting a person's respiration by delivering gas pressure pulses to the person's respiratory system comprising
    a source of gas under pressure,
    a tracheal conduit, one end of which is for insertion into the mouth and throat of the person,
    a jet nozzle disposed in the other end of the conduit for directing gas pressure pulses toward said one end of the conduit,
    a primary delivery conduit coupled between the source of gas and the other end of the tracheal conduit for delivering gas under pressure to the jet nozzle,
    control means coupled to the primary delivery conduit for selectively varying the flow rate through the jet nozzle, and
    an exhaust conduit, one end of which is coupled to the tracheal conduit for carrying away air exhaled by the person,
    wherein said control means comprises
        a control delivery conduit coupled between the primary delivery conduit and the other end of the tracheal conduit for delivering gas under pressure from the primary delivery conduit to the tracheal conduit to a location near the jet nozzle,
        inhalation valve means disposed in the control delivery conduit and responsive to control signals for varying the pressure of gas flowing through the control delivery conduit to the tracheal conduit, and thus the gas flow rate through the jet nozzle, and
        signal means for selectively producing control signals for supplying to the inhalation valve means.

2. Apparatus as in claim 1 further including variable restrictor means disposed in the primary delivery conduit for setting the base flow rate of gas through the primary delivery conduit to the jet nozzle.

3. Apparatus as in claim 1 wherein said inhalation valve means includes first means for varying the pressure of gas in the control delivery conduit at a first selectable rate, and second means for simultaneously varying the pressure of gas in the control delivery conduit at a second selectable rate which is higher than the first rate.

4. Apparatus as in claim 1 further including
    a lumen defined in the tracheal conduit to extend to a point near said one end of the tracheal conduit,
    a pressure detecting conduit coupled to and in communication with the lumen, and
    a pressure transducer coupled to the pressure detecting conduit for developing an indication of the air pressure in the lumen and thus of the air pressure in the person's tracheal airway.

5. Apparatus as in claim 1 further including
    a first anemometer disposed in the primary delivery conduit for measuring the flow rate therein, and
    a second anemometer disposed in the exhaust conduit for measuring the flow rate therein.

6. Apparatus as in claim 5 further including integration means coupled to the first and second anemometers for integrating the flow rates measured by the first and second anemometers to obtain a measure of tidal volume.

7. Apparatus as in claim 5 further including detection means coupled to the first and second anemometers for producing an alarm signal when the flow rates measured by the first and second anemometers differ by a predetermined amount.

8. A method of delivering gas pressure pulses to a person's respiratory system to assist respiration of the person comprising the steps of
    (a) providing a tracheal conduit for inserting one end thereof into the mouth and throat of the person,
    (b) providing a jet nozzle in the other end of the conduit positioned in a direction toward the one end of the conduit, (c) supplying gas under pressure to the jet nozzle to allow jetting of the gas toward the one end of the conduit, (d) selectively varying the flow rate of gas through the jet nozzle, comprising (e) delivering control gas under pressure to the tracheal conduit near the location of the jet nozzle, and (f) simultaneously varying the pressure of the control gas delivered to the tracheal conduit at first and second rates, wherein said first rate is many times greater than said second rate.

* * * * *